US007527899B2

(12) United States Patent
Angell et al.

(10) Patent No.: US 7,527,899 B2
(45) Date of Patent: May 5, 2009

(54) ELECTROLYTIC ORTHOBORATE SALTS FOR LITHIUM BATTERIES

(75) Inventors: Charles Austen Angell, Mesa, AZ (US); Wu Xu, Tempe, AZ (US)

(73) Assignee: Arizona Board of Regents for and on behalf of Arizona State University, Tempe, AZ (US)

( * ) Notice: Subject to any disclaimer, the term of this patent is extended or adjusted under 35 U.S.C. 154(b) by 389 days.

(21) Appl. No.: 10/311,605

(22) PCT Filed: Jun. 18, 2001

(86) PCT No.: PCT/US01/19359

§ 371 (c)(1),
(2), (4) Date: Sep. 3, 2003

(87) PCT Pub. No.: WO01/99209

PCT Pub. Date: Dec. 27, 2001

(65) Prior Publication Data

US 2004/0034253 A1    Feb. 19, 2004

Related U.S. Application Data

(60) Provisional application No. 60/290,864, filed on May 14, 2001, provisional application No. 60/212,231, filed on Jun. 16, 2000.

(51) Int. Cl.
*H01M 6/14* (2006.01)
*H01M 6/18* (2006.01)
*C07F 5/02* (2006.01)
*C01B 35/06* (2006.01)

(52) U.S. Cl. ............... 429/303; 429/307; 429/321; 568/6; 423/293

(58) Field of Classification Search .......... 429/307, 429/303, 321, 322, 324; 568/6; 423/277, 423/293; 544/54
See application file for complete search history.

(56) References Cited

U.S. PATENT DOCUMENTS

| | | | |
|---|---|---|---|
| 2,871,222 A | 1/1959 | Finestone | |
| 3,161,613 A | 12/1964 | Sprung | |
| 3,203,928 A | 8/1965 | Willcockson et al. | |
| 3,259,591 A | 7/1966 | Shepherd | |
| 3,487,045 A | 12/1969 | Shepard et al. | |
| 4,228,270 A | 10/1980 | Kobayashi | |
| 4,620,944 A | 11/1986 | Armand et al. | |
| 4,731,408 A | 3/1988 | Jasne | |
| 5,484,670 A | 1/1996 | Angell et al. | |
| 5,506,073 A | 4/1996 | Angell et al. | |
| 5,660,947 A | 8/1997 | Wuhr | |
| 5,786,110 A | 7/1998 | Angell et al. | |
| 5,807,905 A | 9/1998 | Cunningham et al. | |
| 5,824,433 A | 10/1998 | Angell et al. | |
| 5,849,432 A | 12/1998 | Angell et al. | |
| 5,855,809 A | 1/1999 | Angell et al. | |
| 5,874,616 A | 2/1999 | Howells | |
| 5,962,169 A | 10/1999 | Angell et al. | |
| 6,210,838 B1 | 4/2001 | Fujinami et al. | |
| 6,221,941 B1 | 4/2001 | Strauss et al. | |
| 6,235,433 B1 | 5/2001 | Amano et al. | |
| 6,245,465 B1 | 6/2001 | Angell et al. | |
| 6,485,868 B1 | 11/2002 | Tsujioka et al. | |
| 6,506,516 B1 * | 1/2003 | Wietelmann et al. | ......... 429/188 |
| 6,548,212 B1 | 4/2003 | Heider et al. | |
| 6,924,066 B2 * | 8/2005 | Heider et al. | ............... 429/307 |
| 7,012,124 B2 | 3/2006 | Angell et al. | |
| 2004/0054126 A1 | 3/2004 | Angell et al. | |
| 2006/0189776 A1 | 8/2006 | Angell et al. | |
| 2007/0026295 A1 | 2/2007 | Angell et al. | |
| 2007/0122675 A1 | 5/2007 | Angell et al. | |
| 2007/0298326 A1 | 12/2007 | Angell et al. | |

FOREIGN PATENT DOCUMENTS

| | | |
|---|---|---|
| CA | 2336323 | 1/2000 |
| DE | 198 29 030 | 10/1999 |
| DE | 19829030 | * 10/1999 |
| EP | 708452 | 4/1996 |
| EP | 1035612 | 2/2000 |
| EP | 1 035 612 | 9/2000 |
| EP | 1 074 555 | 7/2001 |
| EP | 1 075 036 | 7/2001 |

(Continued)

OTHER PUBLICATIONS

Carey, Textbook: Organic Chemistry, McGraw Hill, Second Edition, 1992, pp. 50-54, 60-63, 75, 119-121, 140-141, 149-155 & Table.*
Angell. C., et al., "Variations on the Salt-Polymer Electrolyte Theme for Flexible Solid Electrolytes", article, Solid State Ionics, 86-88, 17-28, 1996.
Angell, C. et al., "Rubbery Solid-Electrolytes with Dominant Catronic Transport and High Ambient Conductivity", article, Nature, 362, 137-139, Mar. 11, 1993.
Angell, C., et al., "Fusible Orthoborate Lithium Salt with High Conductivity in Solutions", article, Electrochem Solid State Lett, V 3(8), pp. 366-8, Jun. 14, 2000.

(Continued)

*Primary Examiner*—Raymond Alejandro
(74) *Attorney, Agent, or Firm*—Fish & Richardson P.C.

(57) ABSTRACT

Orthoborate salts suitable for use as electrolytes in lithium batteries and methods for making the electrolyte salts are provided. The electrolytic salts have one of the formulae (I). In this formula anionic orthoborate groups are capped with two bidentate chelating groups, Y1 and Y2. Certain preferred chelating groups are dibasic acid residues, most preferably oxalyl, malonyl and succinyl, disulfonic acid residues, sulfoacetic acid residues and halo-substituted alkylenes. The salts are soluble in non-aqueous solvents and polymeric gels and are useful components of lithium batteries in electrochemical devices.

23 Claims, 8 Drawing Sheets

FOREIGN PATENT DOCUMENTS

| | | |
|---|---|---|
| JP | 1035612 | 7/1989 |
| JP | 1020276 | 1/1991 |
| JP | 3059909 | 3/1991 |
| JP | 3115371 | 5/1991 |
| JP | 11-54151 | 2/1996 |
| JP | 11-185817 | 7/1999 |
| JP | 2000-069202 | 3/2000 |
| JP | 200069202 | 3/2000 |
| JP | 2000-173589 | 6/2000 |
| JP | 2000173343 | 6/2000 |
| JP | 2000-268863 | 9/2000 |
| WO | WO 98/07729 | 7/1997 |
| WO | WO 98/28807 | 12/1997 |
| WO | WO 01/96446 | 12/2001 |

OTHER PUBLICATIONS

Barthel, J., et al., "A New Class of Electrochemically and Thermally Stable Lithium Salts for Lithium Battery Electrolytes", article, J Electrochem Soc, V 143, p. 3572, 1996.

Barthel, J., et al., "A New Class of Electrochemically and Thermally Stable Lithium Salts for Lithium Battery Electrolytes", article, J Electrochem Soc, V 147, p. 21, 2000.

Bessler, E., et al., "Boron complexes with Bis Diorboxylic(Oxalato)Borate and with Bis (Malonato)Borate Acids", article, Zeitschrift fuer Naturforschung, V 37B(8), pp. 1020-5, 1982.

Fujinami, T., et al., "Siloxyaluminate polymers with Li+ ion conductivity", article, Chem Mater, 1997, 9:2236-39.

Hergott, H., et al., "Eine einfache Syntheses von Trichloromethyltrimethylsilan and Carbonsauretrimethylsilylestern", article, Synthesis, V626, 1980.

Krause, L., et al., "Corrosion of aluminum at high voltages in non-aqueous electrolytes containing perfluoroalkysulfonyl imides; new lithium salts for lithium-ion cells", article, J Power Sources, V 68, p. 320, 1997.

MacCallum, J., et al., (eds.), Polymer Electrolytes Reviews, book V1, Elsevier, London, 1987.

Mehta, et al., "Boroxine Ring Containing Polymer Electrolytes", J. Power Sources, 81-82, pp. 724-728, 1999.

Ohno, H., "Molten Salt Type Polymer Electrolytes", Electrochimica Acta, 46, 1407-1400, 2001.

Onishi, K., et al., "Lithium/polyaniline secondary battery composed of transport-numbered-adjusted aluminate solid polymer electrolytes", article, J Electochem Soc, 147(6), 2039-43, 2000.

Onishi, K., et al., "Thioaluminate polymer complexes as single-ionic solid electrolytes", article, Chem Mater 1998, 10, 927-31.

Rawsky, G., et al., "Aluminosilicate/poly(ethylene glycol) copolymers: a new class of polyelectrolytes", article, Chem Mater, 1994, 6, 2008-09.

Sloop, S., et al., "Chemical Reactivity of PF5 and LiPF6 in Ethylene Carbonate/Dimethyl Carbonate Solutions", article, Electrochem & Solid State Lett, V4, p. A42, 2001.

Sun, X., et al., "Polyanionic electrolytes with high alkali ion conductivity", article, J Phys: Condens Matt, 113, 8235-43, 2001.

Xu, W., et al., "A fusible orthoborate lithium salt with high conductivity in solutions", article, Electrochem Solis-State let, 3(8) 366-68, 2000.

Xu, W., et al., "LiBOB and its Derivatives, Weakly Coordinating Anions, and the Exceptional Conductivity of Their Nanaqueous Solutions",article, Electrochem & Solid State Lett, 4, E1, 2001.

Zhang, S., et al., "Molecular and Anionic Polymer System with Micro-Decoupled Conductivities", article, Electrochimica Acta, 45, 12-29, 2000.

Translation of Japanese Office Action for Patent Application No. 2002/503959, mailed Jun. 23, 2004; 5 pages.

Kanbara et al. Ion-conductive polymer electrolyte, its production, and capacitors using it. Apr. 1996. Chem. Abstracts 115:24138.

International Search Report for PCT/US01/41009, mailed Sep. 14, 2001; 2 pages.

International Preliminary Examination Report for PCT/US01/41009, mailed Jan. 28, 2003; 5 pages.

International Search Report for PCT/US01/19338, mailed Nov. 29, 2001; 1 page.

International Search Report for WO 01/99209, mailed Jan. 23, 2002; 4 pages.

Angell et al., "Li-conducting ionic rubbers for lithium battery and other applications," Solid State Ionics, vol. 69, p. 343-353 (1994).

Angell, C.A., "Fast Ion Motion in Glassy and Amorphous Materials," Solid State Ionics, 9 & 10, p. 3-16 (1983).

Armand, M. et al., "Perfluorosulphonimide Salts as Solute for Polymer Electrolytes," Proceedings of the Second International Symposium onPolymer-Electrolytes, B. Scrosati, Editor, Elsevier, New York, p. 91-97 (1990).

Armand, M., "A History of Polymer Electrolytes," Solid State Ionics, 69: p. 309-319 (1994).

Bruce et al., "The determination of transference numbers in solid polymer electrolytes using the Hittorf method," Solid State Ionics, 53-56, p. 10807-1094 (1992).

Ito et al, "Effect of Terminal groups on the ionic conductivity of $\alpha$, $\omega$-discharge poly(ethylene oxide) oligomers," Solid State Ionics, 86-88, p. 325-328 (1996).

Ito et al., "Polyether/salt hybrid (IV). Effect of benzenesulfonate group(s) and PEO molecular weight on the bulk ionic conductivity," Electrochimica. Acta, 42, p. 1561-1570 (1997).

Ohno et al., "Ionic Conductivity of Molten Sants Formed by Polyether/Salt Hybrids," Chemistry Lerters, p. 15-16 (1998).

Xu et al., "LiMOB, an unsymmetrical non-aromatic orthoborate salt for non-aqueous solution electrochemical applications," J. Electrochem. Soc 151 (4): A632-A638 2004.

Xu et al., "Novel Polyanionic Solic Electrolytes with Weak Coulomb Traps and Controllable Caps and Spacers," Chem Mater. 14: 401-409 (2002).

Xu et al., "Preparation and characterization of novel "polyMOB" polyanionic solid electrolytes with weak coulomb traps," State State Ionics 147: 295-301 (2002).

Xu, W.a nd C.A. Angell, "Solvent-Free Electrolytes with Aqueous Solution-Like Conductivities," Science 302: 422-eoa (Oct. 17, 2003).

Xu et al., "LiBOB as Salt for Lithium-Ion Batteries," Electrochemical and Solid-State Letters 5(1): A26-A29 (2002).

Xu, K. and C.A. Angell, "Non-Crystallizing Molten Salt and Ionic Rubber Electrolytes with Wide Electrochemical Windows," Materials Research Society Symposium Proceedings, Solid State Ionicsm IV, Symposium held Nov. 28-Dec. 1, 1994, Boston, Massachusetts, U.S.A., vol. 369, p. 505-510 (1995).

Xu, K. and C.A. Angell, "Synthesis and Characterization of Lithium Sulfonates as Components of Molten Salt Electrolytes," Electrochimica. Acta vol. 40, p. 2401-2403 (1995).

Mehta et al. Electrochemica Acta 45:1175(2000).

Onishi et al. "Thioaluminate polymer complexes as single-ionic solid electrolytes." 1998. Chem. Abstracts 128:224296.

Rawsky et al. "Aluminosilicate/Poly(ethyleneglycol) copolymers: A new class of Polyelectrolytes," 1994. Chem. Abstracts 121:281368.

Nose et al. "Anchoring coatings in electrically conducting plastic films." Mar. 1991. Chem. Abstracts. 115:94059.

Xu et al., Ionic Liquids of Chelated Orthoborates as Model Ionic Glassformers, J. Phys. Chem. 107: 11749-11756 (2003).

Kanbara et al. Ion-conductive polymer electrolyte, its production, and capacitors using it. Apr. 1996. Chem. Abstracts125:24138. See EP708452.

Saito et al. Transparent electrically conductive resin compositions and laminates thereof. May 1991. Chem Abstracts 115:184646.

Yamaguchi et al. "Copper poweder containing electrically conductive coatings." Jan. 1989. Chem. Abstracts. 112:8780.

* cited by examiner

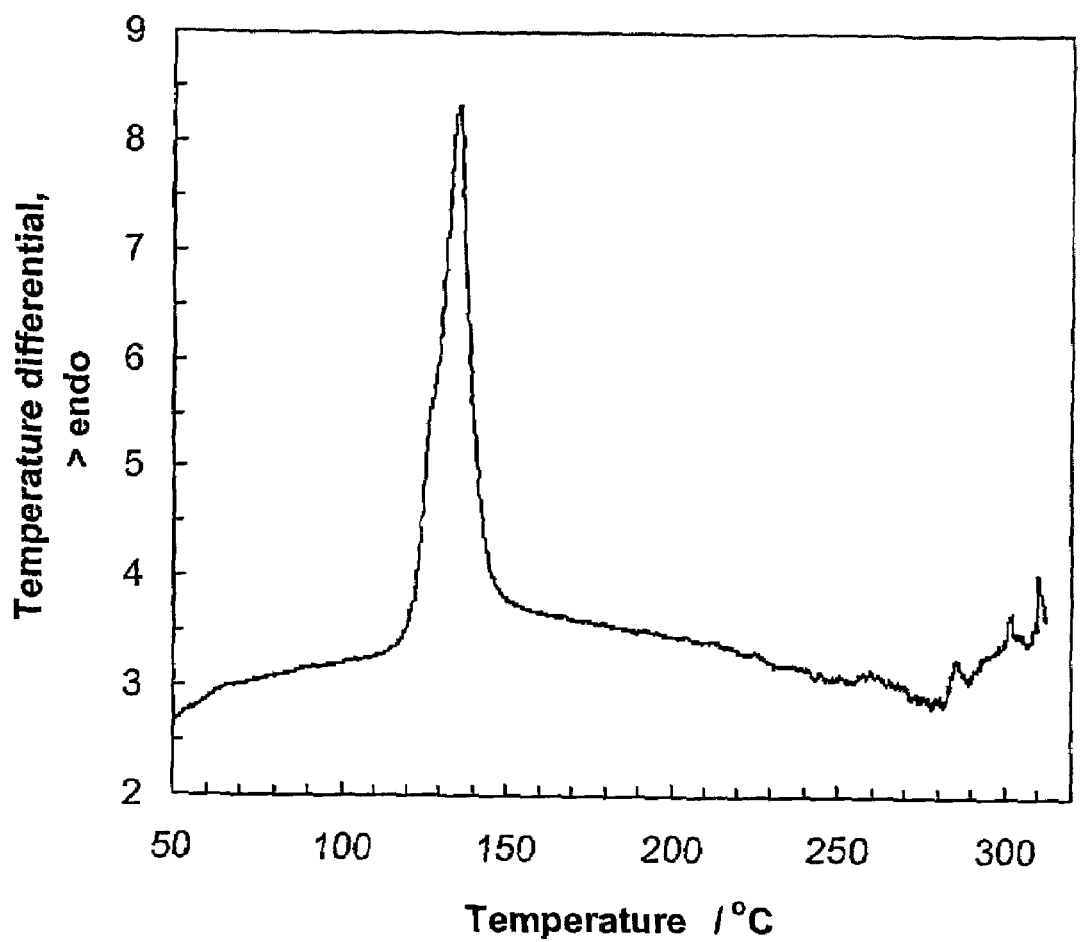
Figure 1. DTA trace thermogram at 10°C min$^{-1}$ for pure LiB[OC(CF$_3$)$_2$]$_4$ or LiBPFPB, showing fusion at 120°C and decomposition at 280°C.

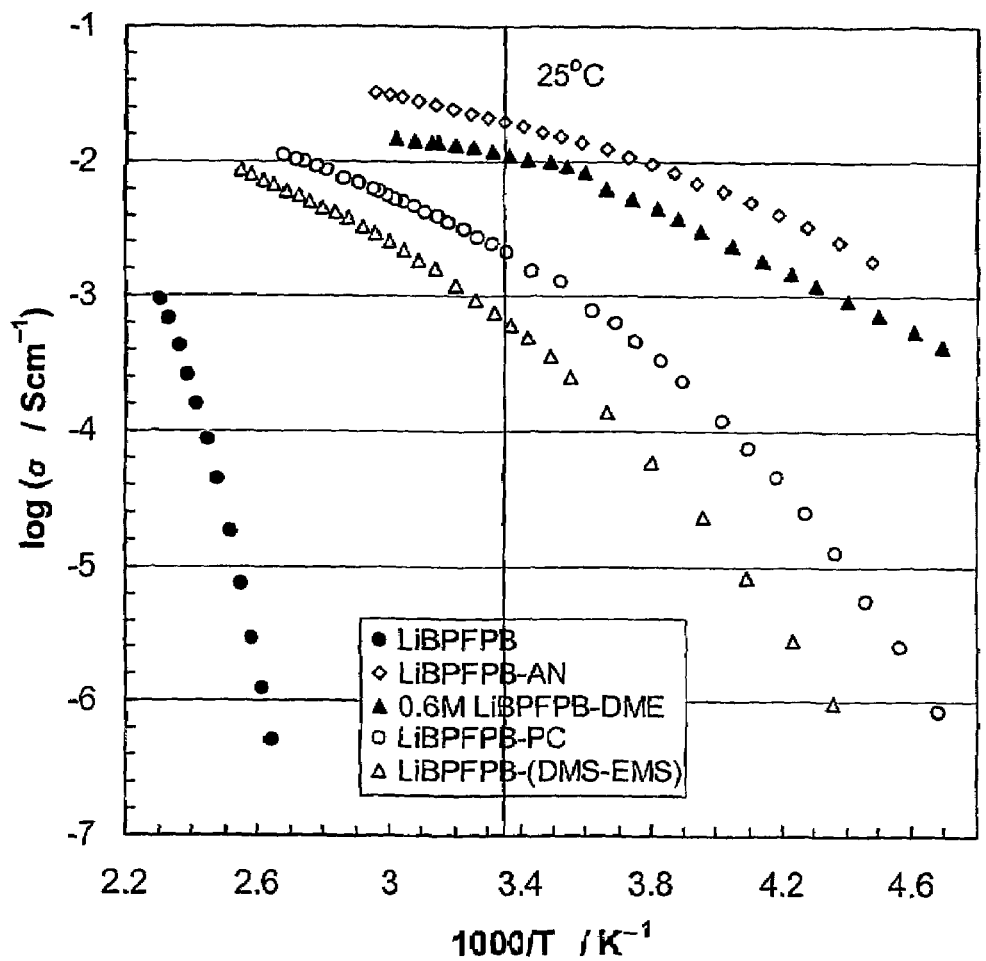
Figure 2. Ionic conductivities of LiBPFPB and its solutions in 1M acetontrile (AN), 0.6M DME, 1M PC and 1M DMS-EMS (15:85 by weight).

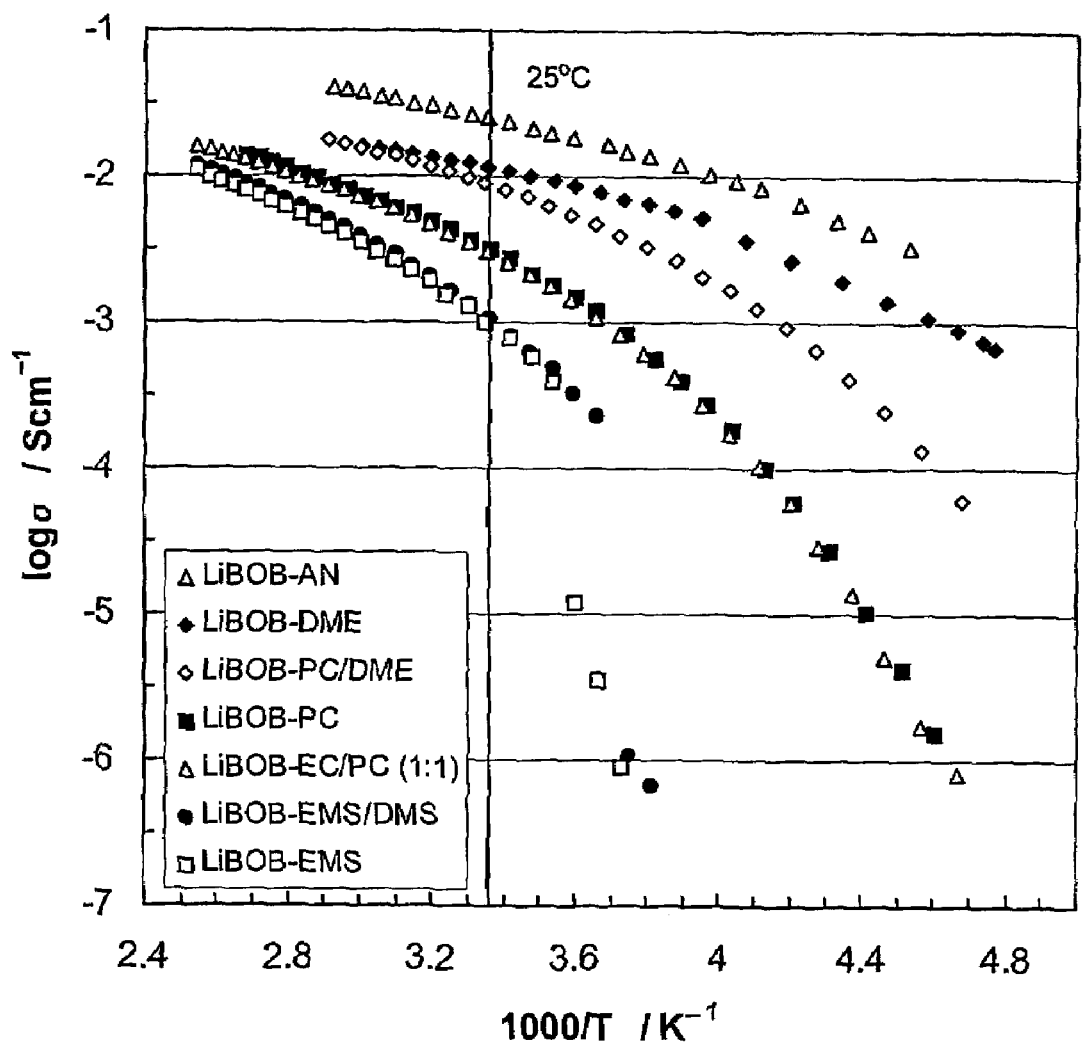
Figure 3. Ionic conductivities of 1M LiBOB solutions.

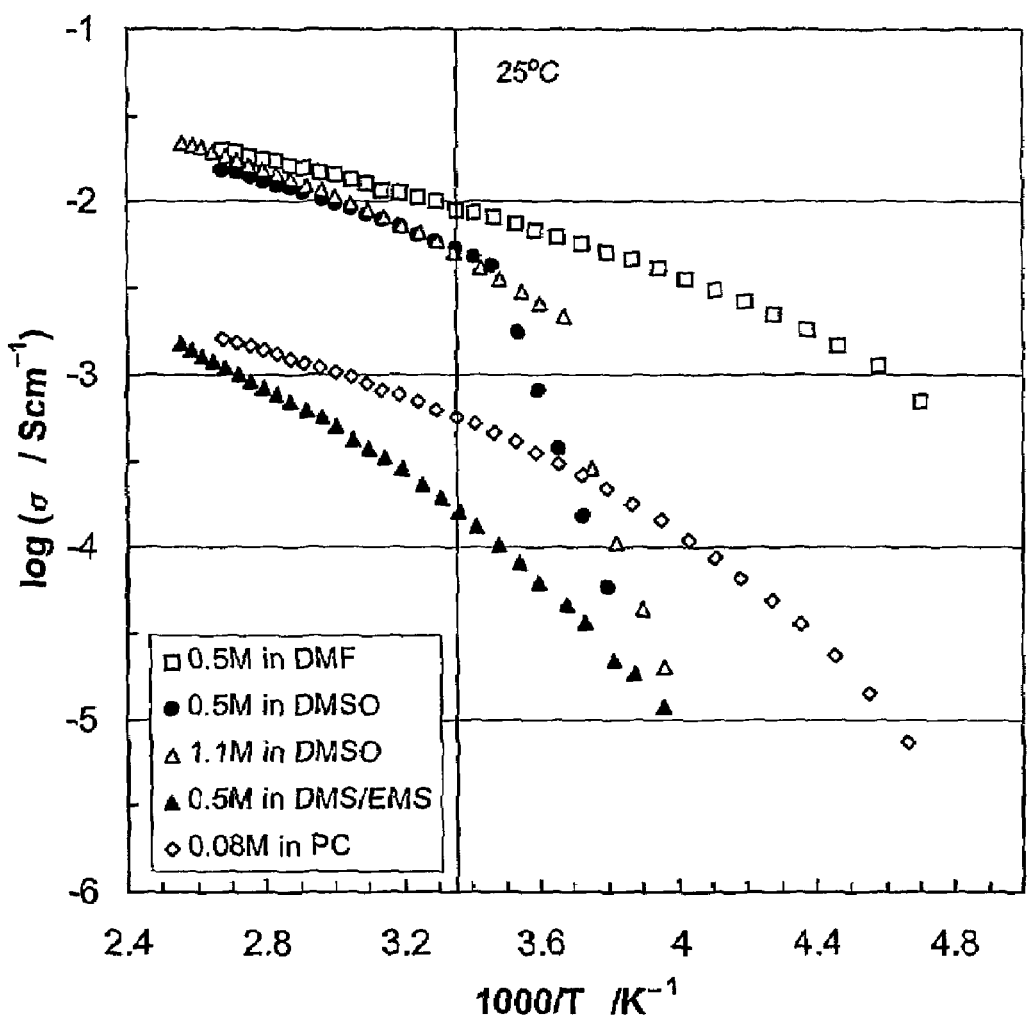
Figure 4. Ionic conductivities of LiBMB solutions.

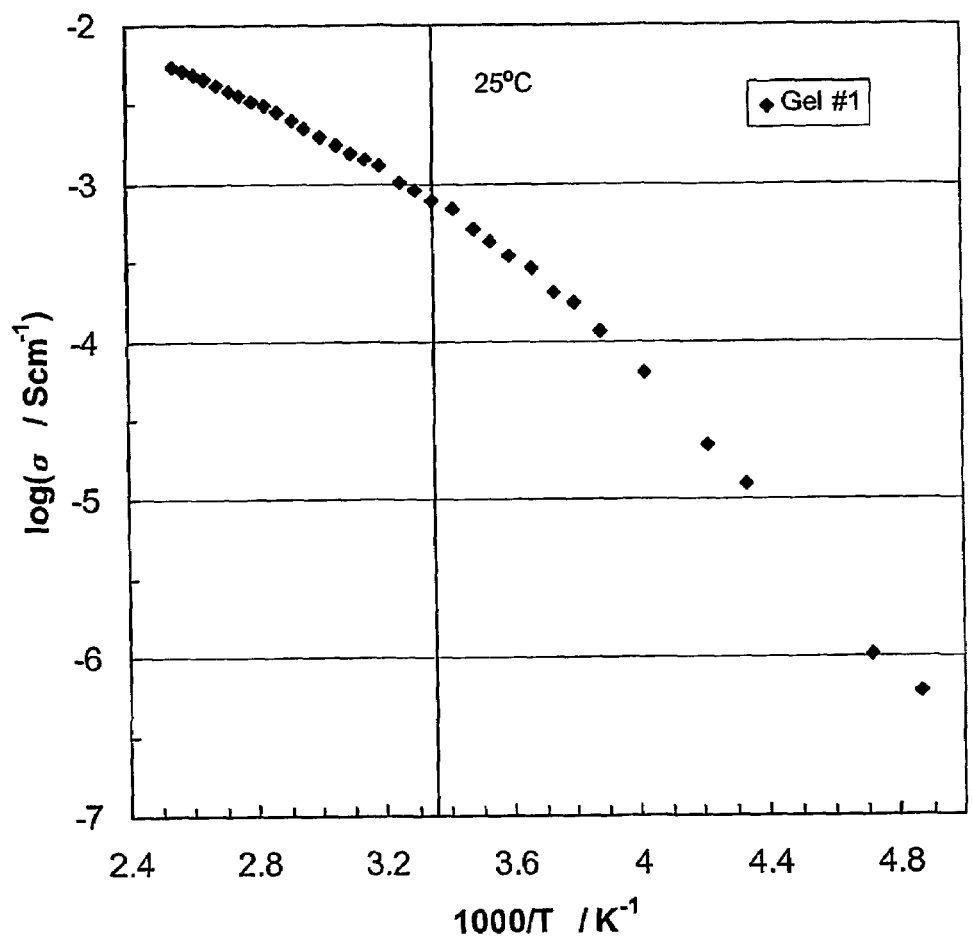
Figure 5. Temperature dependence of ionic conductivity of a gel electrolyte (Gel #1) with composition of 21.17 PMMA (MW 996,000), 7.88 LiBOB, 35.48 EC and 35.47 PC.

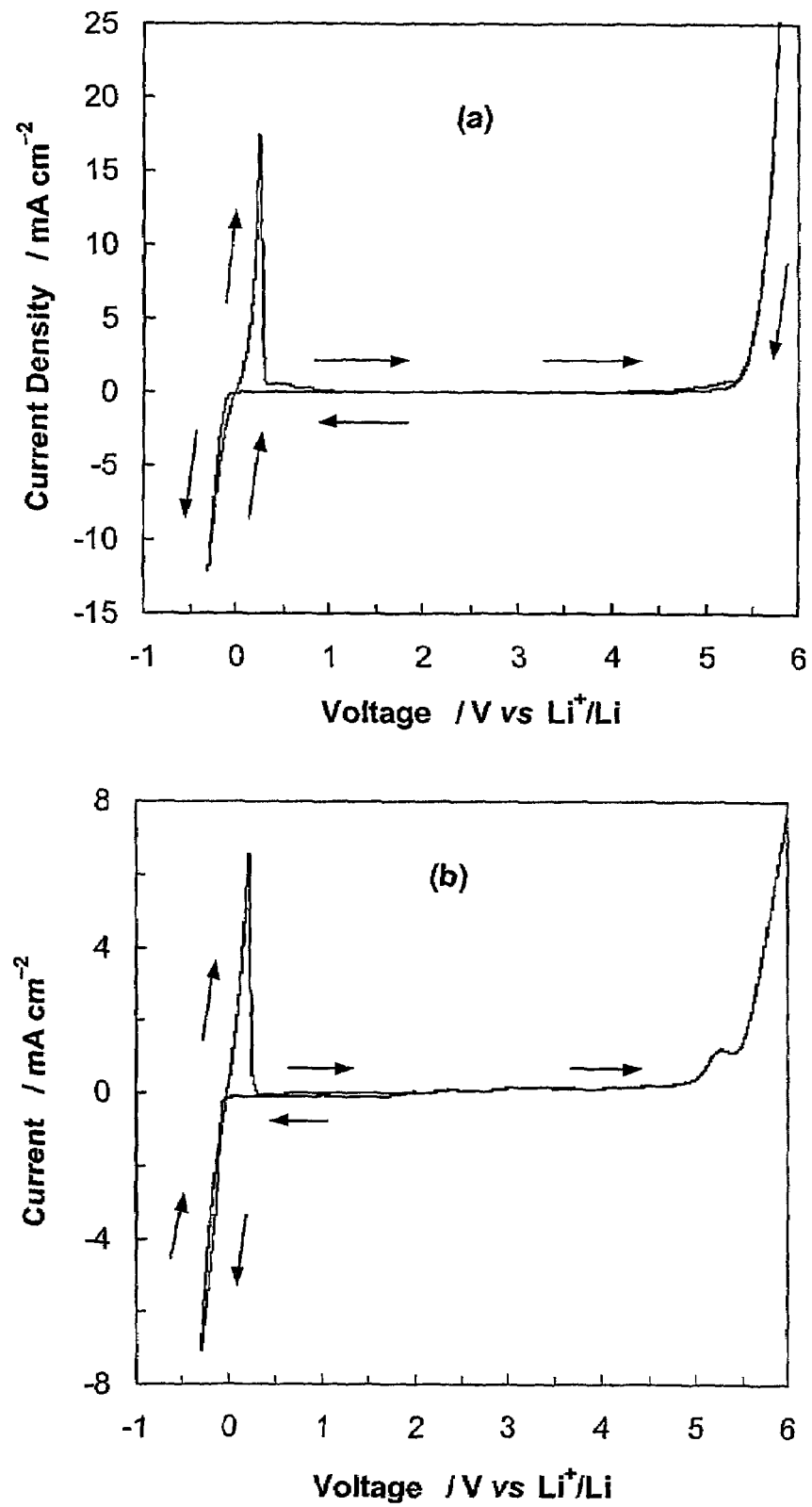
Figure 6. Cyclic voltammograms of LiBPFPB in DME and PC solutions, parts (a) and (b) respectively, in a cell with Pt as working electrode and lithium as counter and reference electrodes. Working electrode area: $4.91 \times 10^{-4}$ cm$^2$; Scan rate: 1 mVs$^{-1}$.

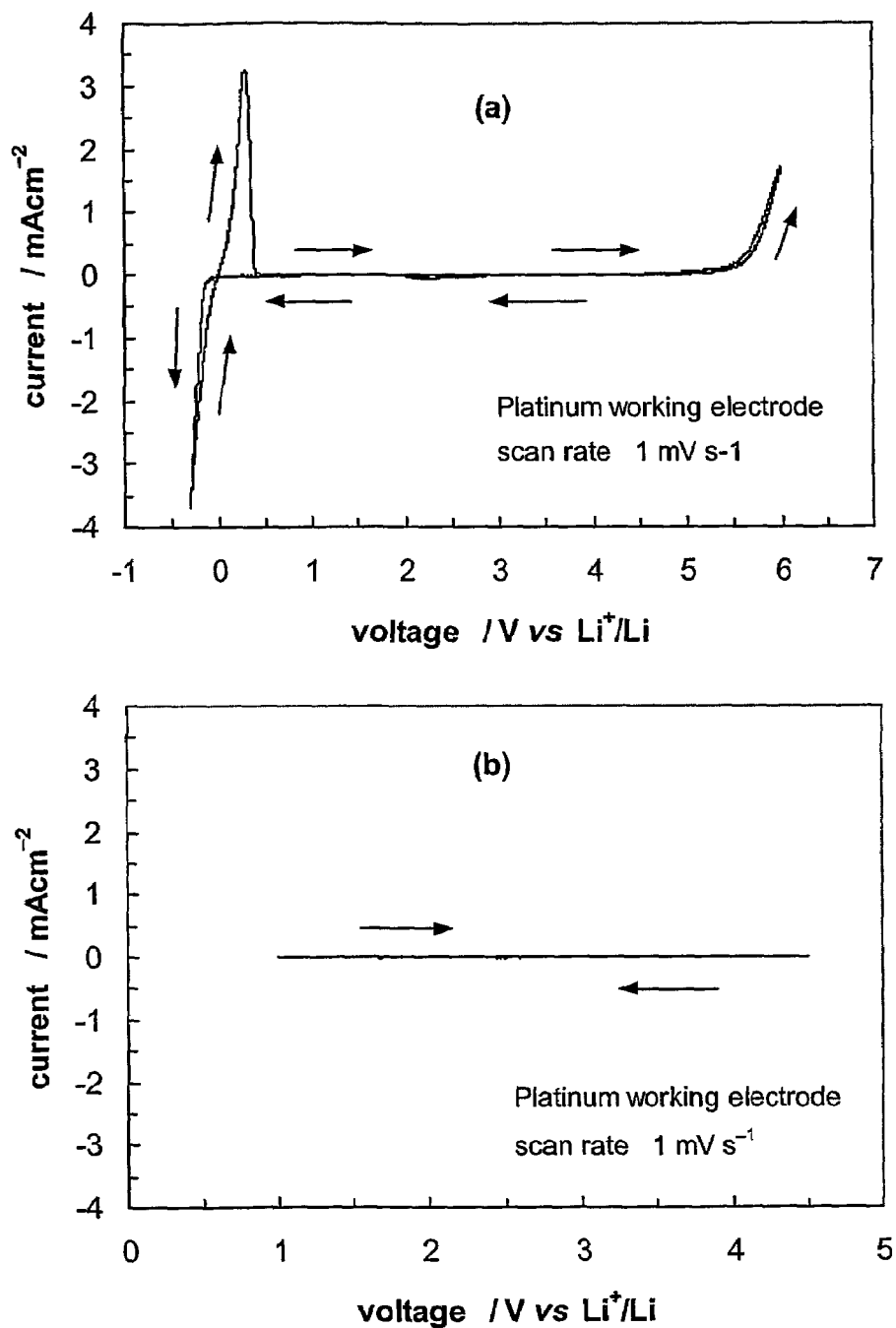
Figure 7. Lithium deposition-stripping process and electrochemical stability of 1M LiBOB-PC solution scanned at 1 mV s$^{-1}$ in the voltage range of (a) −0.3 ~ 6 V and (b) 1 ~ 4.5 V vs. Li$^+$/Li at room temperature. The area of platinum wire working electrode is 4.91 × 10$^{-4}$ cm$^2$. The "window" is at least 4.5 V.

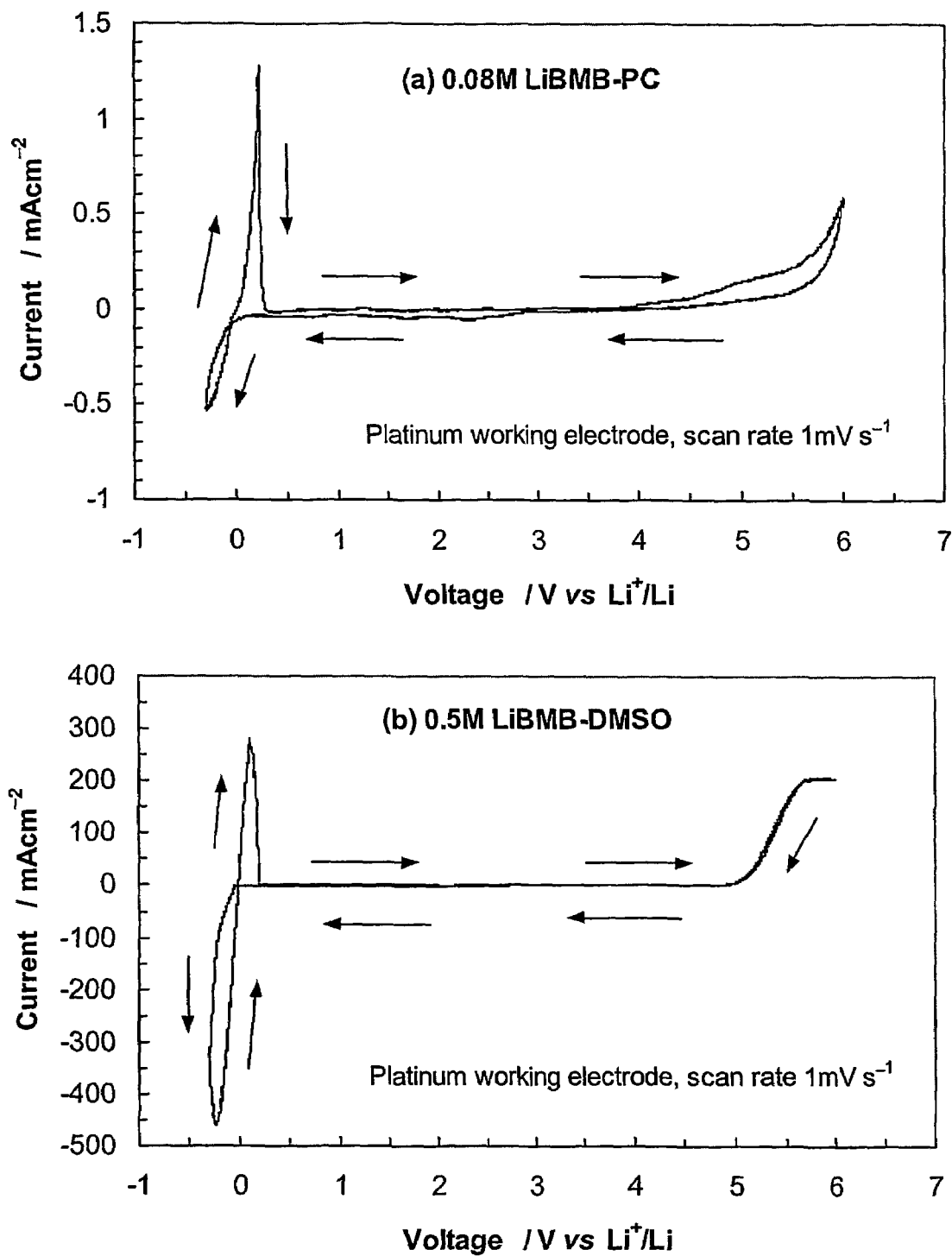
Figure 8. Electrochemical stability of LiBMB solutions in PC (a) and DMSO (b), respectively. Area of platinum working electrode 4.91 × $10^{-4}$ cm$^2$.

ELECTROLYTIC ORTHOBORATE SALTS FOR LITHIUM BATTERIES

RELATED APPLICATIONS

This application is a U.S. National Stage Application filed under 35 U.S.C. 371 claiming priority from the International Application Serial No. PCT/US01/19359 filed Jun. 18,2001 and published in English as WO 01/99209 A2 on Dec. 27,2001, which claims priority from U.S. Provisional Patent Application Ser. No. 60/212,231 filed Jun. 16,2000 and U.S. Provisional Patent Application Ser. No. 60/290,864 filed May 14, 2001, which applications and publication are incorporated herein by reference.

Financial assistance for this project was provided by the U.S. Government through the Department of Energy under Grant Nos. DEFG0393ER14378-003 and DEFG0395ER45541. Therefore, the United States Government may own certain rights to this invention.

INTRODUCTION

1. Technical Field

The present invention relates to novel electrolytic salts having high conductivity suitable for use in lithium batteries, especially secondary lithium batteries.

2. Background

Lithium batteries supply energy to a growing number of portable electrochemical devices and are a promising energy source for larger applications such as electric automobiles. Accordingly, lithium batteries are the subject of intense research and the effort to improve performance continues.

A major area of interest has been in the field of electrolytes for lithium cells where electrolytes with high ionic conductivity, wide electrochemical stability window and good lithium ion transport number have been the goal. Electrolytic solutions are generally prepared by dissolving a highly-conductive salt in a proper non-aqueous solvent or a mixture of several solvents and polymer electrolytes are generally prepared by dissolving a highly-conductive salt in a polymer, usually an ether polymer, to make solid polymeric electrolytes (SPE). Examples of suitable electrolytes have been disclosed in U.S. Pat. Nos. 5,849,432, 5,824,433, 5,660,947.

The electrolyte solute lithium hexafluorophosphate ($LiPF_6$) is currently the electrolytic salt used commercially in lithium batteries (1), but this electrolyte exhibits a thermal instability that restricts its use to ambient temperature (2). Investigations of weakly coordinating anion groups continue to spur the development of new salts suitable for inclusion into electrolytic solutions and SPE (3,4). In the past ten years many novel kinds of electrolytic salts, showing high ionic conductivity, large electrochemical stability and high thermal stability in solutions, have been reported. Howelss et al. disclose substituted imides in U.S. Pat. No. 5,874,616. Various chelatoborates have been studied (4.5) and a highly conductive salt, lithium bis(oxalato)borate (LiBOB), has recently been disclosed in DE 19829030. This salt has been further characterized and shows promise as an electrolytic solution in lithium batteries (7). Heide et al. disclose orthoborates as additives in electrolytes for improved performance of electrochemical cells in European Patent Application 1,035,612.

Accordingly, novel electrolytic salts are still being sought.

3. Relevant Literature

1. S. E. Sloop, J. K. Pugh, S. Wang, J. B. Kerr, and K. Kinoshita, *Electrochem. and Solid State Lett.*, 4, A42 (2001).
2. L. J. Krause, W. Lamanna, J. Summerfield, M. Engle, G. Korba, and R. Atanasoski, *J. Power Sources,* 68, 320 (1997).
3. C. A. Angell, C. Liu and G. Sanches, Nature 362, 137-139, Mar. 11, 1993.
4. S. S. Zhang, Z. Chang, K. Xu and C. A. Angell, Electrochim. Acta 45, 12-29 (2000).
5. J. Barthel, A. Schmid and H. J. Gores, *J. Electrochem. Soc.,* 147, 21 (2000).
6. W. Xu, C. A. Angell, *Electrochem. Solid-State Lett.,* 3(8), 366-368 (2000).
7. W. Xu, C. A. Angell, *Electrochem. Solid-State Lett.,* 4(1), E1-E4 (2001).

BRIEF DESCRIPTION OF THE DRAWINGS

FIG. 1 illustrates DTA trace thermogram at 10° C. min$^{-1}$ for pure $LiB[OC(CF_3)_2]_4$ or LiBPFPB, showing fusion at 120° C. and decomposition at 280° C.

FIG. 2 illustrates ionic conductivities of LiBPFPB and its solutions in 1M acetontrile (AN), 0.6M DME, 1M PC and 1M DMS-EMS (15:85 by weight).

FIG. 3 illustrates ionic conductivities of 1M LiBOB solutions.

FIG. 4 illustrates ionic conductivities of LiBMB solutions.

FIG. 5 illustrates temperature dependence of ionic conductivity of a gel electrolyte (Gel #1) with composition of 21.17 PMMA (MW 996,000), 7.88 LiBOB, 35.48 EC and 35.47 PC.

FIG. 6 illustrates cyclic voltammograms of LiBPFPB in DME and PC solutions, parts (a) and (b) respectively, in a cell with Pt as working electrode and lithium as counter and reference electrodes. Working electrode area: $4.91 \times 10^{-4}$ cm$^2$; Scan rate: 1 mVs$^{-1}$.

FIG. 7 illustrates lithium deposition-stripping process and electrochemical stability of 1M LiBOB-PC solution scanned at 1 mV s$^{-1}$ in the voltage range of (a) –0.3~6 V and (b) 1~4.5 V vs. Li$^+$/Li at room temperature. The area of platinum wire working electrode is $4.91 \times 10^{-4}$ cm$^2$. The "window" is at least 4.5 V.

FIG. 8 illustrates electrochemical stability of LiBMB solutions in PC (a) and DMSO (b), respectively. Area of platinum working electrode $4.91 \times 10^{-4}$ cm$^2$.

SUMMARY OF THE INVENTION

It has been discovered that certain orthoborate salts suitable for use as electrolytes in lithium batteries may be readily prepared. The salts comprise orthoborate anionic groups capped with two bidentate chelating groups. The capping groups may be the same or different. The orthoborate capping groups are preferably certain dibasic acid residues, i.e., diacyl, most preferably oxalyl, malonyl and succinyl. Certain other capping groups comprise disulfonic acid residues and sulfoacetic acid residues. Certain other capping groups comprise halo-substituted alkylenes.

Methods for making the conductive salts are provided. In a preferred method, an alkoxy orthoborate salt and the di(trimethylsilyl) dibasic acid ester of the chelate are provided. The orthoborate salt and the silyl ester are combined to form the capped borate salt. In another preferred method, the acidic chelate is provided and is reacted with boric acid under basic conditions to form the capped borate salt.

The conductivity in non-aqueous solvents, the electrochemical window and thermal stability of the present orthoborate salts make them excellent electrolytes for electrochemical devices. The electrolytic salts have been incorporated into conductive gels suitable for use in lithium batteries, especially secondary lithium batteries.

DETAILED DESCRIPTION OF THE PREFERRED EMBODIMENTS

The tetragonally coordinated orthoborate anion is a weak Lewis base that provides four oxygen atoms for binding to suitable ligands. The choice of ligand determines the bonding strength of the Lewis base for its counter ion. It has been discovered that highly conductive electrolytes may be prepared by capping the orthoborate anion with certain electron withdrawing ligands that delocalize the electron density of the orthoborate anion. The capping ligands form stable bonds to the orthoborate and stable salts with good electrochemical window and stability above ambient temperature result.

The salts comprise orthoborate anionic groups capped with two bidentate chelating groups. In certain instances, the capping groups are the same. In certain other instances, the capping groups are different. The orthoborate capping groups are preferably bidentate chelates that bind pairwise—i.e., each chelate comprises two reactive groups and each reactive group binds an oxygen of the tetragonal orthoborate anion. Preferred capping groups are from dicarboxylic acids and R-substituted dicarboxylic acids, most preferably oxalic acid, malonic acid and succinic acid. Certain other preferred capping groups comprise disulfonic acid, R-substituted disulfonic acid, sulfoacetic acid, and R substituted sulfoacetic acid, preferably fluoro-substituted sulfoacetic acid wherein R is preferably hydrogen, alkyl or halo. In certain other instances the capping group may be a halo-substituted alkylene, preferably lithium bis(tetrafluoroethylenediolato)borate $LiB(OCF_2CF_2O)_2$, lithium bis(hexafluoropropylenediolato)borate $LiB[OCF(CF_3)CF_2O]_2$ and lithium bis[1,2-tetrakis(trifluoromethyl)ethylenedialato(2-)O,O']borate or lithium bis(perfluoropinacolato)borate $LiB[OC(CF_3)_2C(CF_3)_2O]_2$ or $LiB[OC(CF_3)_2]_4$ or LIBPFPB. The perfluoropinacolato salt was disclosed by Xu, W. and Angell, C. A. in *Electrochemical and Solid-State Letters*, 3(8), 366-368 (2000) and is herein incorporated by reference.

The electrolyte salts of the present invention have one of the formulae:

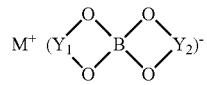

$Y_1$ and $Y_2$ are each bound to a pair of said oxygens and are selected from the group comprising $XC-(CR_2)_aCX$ wherein a is 0 to 4 and X is =O, —C=N, $CR'_3$ or $R'_3$ wherein R' is halo, R is hydrogen, alkyl, cyano, or halo provided that when a is 0 and X is $CF_3$ or =O, $Y_1$ is not $Y_2$; and.; $O_2S(CR_2)_bSO_2$ and $OC(CR_2)_bSO_2$ wherein b is 1 to 4 and R is hydrogen, alkyl, or halo, wherein $Y_1$ and $Y_2$ are the same or different in each occurrence;

$M^+$ is a metal ion selected from the Group I or Group II elements, preferably from Group I and most preferably lithium.

In an important aspect of the present invention, methods for preparing the electrolytic salts are presented. In a preferred method, an alkoxy orthoborate salt, preferably lithium tetramethanolatoborate and the di(trimethylsilyl) ester of the chelate are provided. Thus, for example, when the bis(oxalato)borate salt is desired, di(trimethylsilyl) oxalate is provided. When bis(methylenedisulfonato)borate salt is desired, di(trimethylsilyl)methylenedisulfonate is provided. When mixed capping groups are desired, as in the (oxalatomalonato)borate salt, a mixture of di(trimethylsilyl) malonate and di(trimethylsilyl) oxalate are provided. All these salts may be prepared by methods known in the art as described in the following examples.

In another preferred method, the acid form of the capping group is combined with boric acid and a metal base and allowed to react to form the capped orthoborate salt. In this method, the metal is preferably to be a metal chosen from the Group I group of elements, most preferably lithium. Thus, for example, when an orthoborate salt comprising the capping groups malonyl is desired, (e.g., lithium bis(malonato)borate), double molar amounts of malonic acid and mono molar amount of, boric acid and lithium hydroxide are combined and caused to react. When an orthoborate salt comprising different capping groups is desired, e.g., lithium (malonatooxalato) borate, equal molar amounts of malonic acid, oxalic acid, boric acid and lithium hydroxide are provided. When an orthoborate salt comprising the capping groups sulfoacetyl is desired, double molar amounts of sulfoacetic acid, and mono molar amount of boric acid and lithium hydroxide are provided.

In another aspect of the present invention, conductive electrolytic solutions of he lithium orthoborate salts are provided. Preferred non-aqueous solvents are carbonate or non-carbonate plasticizers or their mixtures. Suitable carbonate plasticizers are, for example, ethylene carbonate (EC), propylene carbonate (PC), butylene carbonate (BC), dimethyl carbonate (DMC) and diethyl carbonate (DEC). Suitable non-carbonate plasticizers are 1,2-dimethoxyethane (DME), 1,2-diethoxyethane (DEE), dimethylsulfoxide (DMSO), dimethyl sulfone (DMS), ethylmethylsulfone (EMS), γ-butyrolactone (BL). Preferred plasticizer mixtures are EC-PC, EC-DMC, EC-DMC-DEC, and PC-DME. The conductivities of certain preferred embodiments of the present invention in the presence of certain of these plasticizers are given in FIGS. 2, 3 and 4.

In yet another aspect of the present invention, gel electrolytes comprising certain embodiments of the present salts are given. A salt is dissolved in a solvent as disclosed hereinabove and the solution is added to a high molecular weight polymer. Suitable polymers are those polymers, poly(methyl methacrylate, EMMA), or polyacrylonitrile, (PAN) for example, that are generally used in solid polymeric electrolyte (SPE) for electrochemical applications.

An important aspect of the present invention presents the battery performance of the orthoborate electrolytes of the present invention. Batteries comprising a lithium anode and a composite cathode membrane with certain electrolytic salts of the present invention exhibit good performance and multiple galvanostatic charge-discharge cyclic curves.

These and other features, aspects and advantages of the present invention will become better understood with reference to the following descriptive examples.

EXAMPLE 1

This example illustrates the synthesis of a lithium salt of an orthoborate in which the four boron oxygens are pairwise connected by two oxalyl groups, to give an anion of bis(oxalato)borate. This compound has a formula lithium bis(oxalato)borate, LiBOB. The preparation included the following three steps.

(1) Lithium tetramethanolatoborate, $LiB(OCH_3)_4$, was synthesized following the procedures described by Barthel et al. (J. Barthel, R. Buestrich, E. Carl and H. J. Gores, *J. Electrochem. Soc.*, 143, 3572 (1996).) The yield was 95%.

NMR spectra in DMSO-d$_6$: $^1$H, δ3.16 ppm (s); $^{13}$C, δ48.56 ppm; $^7$Li (referenced to LiNO$_3$ in D$_2$O), δ1.05 ppm; and $^{11}$B (referenced to BF3 Et$_2$O in CDCl$_3$), δ7.84 ppm.

(2) Di(trimethylsilyl) oxalate, DTMSO, was synthesized according to the method by Hergott and Simchen (H. H. Hergott and G. Simchen, *Synthesis*, 626 (1980).), by reacting 0.20 mol oxalic acid and 0.46 mol chlorotrimethylsilane in anhydrous 1,2-dichloroethane at around 70° C. till all acid had reacted (about 3 days). After evaporating the low boiling point solvent and unreacted chlorotrimethylsilane, the residual was distilled under high vacuum. The colorless fraction of b.p. 65-68° C./0.5 μmmHg was collexted, which crystallized quickly on cooling. The yield was 71%. NMR spectra in CDCl$_3$: $^1$H, δ0.36 ppm (s); $^{13}$C, δ158.31 and −0.51 ppm; and $^{29}$Si (referenced to TMS in CDCl$_3$), δ7.42 ppm.

(3) LiBOB was obtained by stirring 0.025 mol lithium tetramethanolatoborate, LiB(OCH$_3$)$_4$, and 0.050 mol di(trimethylsilyl) oxalate (DTMSO) in a large amount of anhydrous acetonitrile (AN) in an oil bath at 45-50° C. overnight. The white solid LiB(OCH$_3$)$_4$ disappeared and the solution became slightly cloudy. After rotary-evaporating all low boiling point compounds (methoxytrimethylsilane formed according to scheme 1, and solvent (AN acetonitrile) at a temperature below 50° C. under reduced pressure, the crude solid product was dried in an oven at 75° C. under high vacuum for 24 hours. LiBOB was then recrystallized from boiling acetonitrile/toluene (1:1 mixture), subsequent cooled to −20° C. After filtration, the product was dried in a vacuum oven at 80° C. for 48 hours to give a white solid, in high yield, around 92%. NMR spectra in DMSO-d$_6$: $^1$H, only for solvent; $^{13}$C, δ158.10 ppm; $^7$Li (referenced to LiNO$_3$ in D$_2$O), δ0.98 ppm; and $^{11}$B (referenced to BF$_3$ Et$_2$O in CDCl$_3$), δ12.20 ppm. Elemental analysis for C: found 24.68%, calculate (for C$_4$O$_8$BLi) 24.74%.

EXAMPLE 2

This example illustrates the synthesis of a lithium salt of an orthoborate in which the four boron oxygens are pairwise connected by two malonyl groups, to give an anion of bis (malonato)borate. This compound has a formula lithium bis (malonato)borate, LiBMB. The preparation included the similar three steps in Example 1, just using malonic acid to replace oxalic acid and di(trimethylsilyl) malonate (DTMSM) to replace di(trimethylsilyl) oxalate (DTMSO).

DTMSM was a colorless liquid of b.p. 70-72° C./0.2 mmHg. The yield was 60% NMR spectra in CDCl$_3$: $^1$H, δ3.27 ppm (s, 2H) and −0.24 ppm (s, 18H); $^{13}$C, δ166.96, 44.82 and −0.49 ppm; and $^{29}$Si (referenced to TMS in CDCl$_3$), δ25.79 ppm.

LiBMB was recrystallized from anhydrous acetone with a yield about 90%. NMR spectra in DMSO-d$_6$: $^1$H, δ3.39 ppm; $^{13}$C, δ166.03 and 38.56 ppm; $^7$Li (referenced to LiNO$_3$ in D$_2$O), δ1.04 ppm; and $^{11}$B (referenced to BF$_3$.Et$_2$O in CDCl$_3$), δ8.26 ppm. Elemental analysis: found C 32.15%, H 2.11%, calculate (for C$_6$H$_4$O$_8$BLi) C 32.43%, H 1.80%.

EXAMPLE 3

This example illustrates another way to synthesize the lithium salt of an orthoborate in which the four boron oxygens are pairwise connected by two malonyl groups, to give an anion of bis(malonato)borate, LiBMB. The preparation was similar to the second step in Example 1. 0.2 mol malonic acid, boric acid and 0.1 mol lithium hydroxide monohydrate were dissolved in some distilled water and boiled in an oil bath of around 130° C. overnight to evaporate all water. The residual solid was further dried in a vacuum oven at 100° C. for one day and then recrystallized in anhydrous acetone to give a white solid, which was dried in a vacuum oven at 100° C. for 48 hours. The characterization results were the same as in Example 2.

EXAMPLE 4

This example illustrates the synthesis of a lithium salt of an orthoborate in which the four boron oxygens are pairwise connected by two succinyl groups, to give an anion of bis (succinato)borate. This compound has a formula lithium bis (succinato)borate, LiBSB. The preparation includes three steps similar to those in Example 1, just using succinic acid to replace oxalic acid and di(trimethylsilyl) succinate (DTMSS) to replace di(trimethylsilyl) oxalate.

EXAMPLE 5

This example illustrates another way to synthesize the lithium salt of an orthoborate in which the four boron oxygens are pairwise connected by two succinyl groups, to give an anion of bis(succinato)borate, LiBSB. The preparation was similar to that in Example 3, just using succinic acid to replace malonic acid.

EXAMPLE 6

This example illustrates the synthesis of a lithium salt of an orthoborate in which the four boron oxygens are pairwise connected by one malonyl group and one oxalyl group, to give an anion of malonato oxalato borate. This compound has a formula lithium (malonato oxalato) borate, LiMOB. The preparation included the similar steps in Example 1, just by stirring equal molar lithium tetramethanolatoborate, LiB (OCH$_3$)$_4$, di(trimethylsilyl) malonate (DTMSM) and mol di(trimethylsilyl) oxalate (DTMSO) in anhydrous acetonitrile at 45-50° C. overnight. LiMOB was recrystallized from anhydrous acetonitrile with a yield about 86%. NMR spectra in DMSO-d$_6$: $^1$H, δ3.52 ppm; $^{13}$C, δ165.56, 158.49 and 38.35 ppm; $^7$Li (referenced to LiNO$_3$ in D$_2$O), δ0.99 ppm; and $^{11}$B (referenced to BF$_3$.Et$_2$O in CDCl$_3$), δ9.91 ppm (integral 95.5%) and 12.03 ppm (integral 4.5%), which indicated the presence of small amount of lithium bis(oxalato)borate, LiBOB, as an impurity in the product. LiBOB may be removed by the treatment of anhydrous tetrahydrofuran to give a pure LiMOB.

EXAMPLE 7

This example illustrates another way to synthesize the lithium salt of an orthoborate in which the four boron oxygens are pairwise connected by one malonyl group and one oxalyl group, to give an anion of malonato oxalato borate, LiMOB. The preparation was similar to that in Example 3, by boiling the aqueous solution of equal moll malonic acid, oxalic acid, boric acid and lithium hydroxide monohydrate in an oil bath of around 130° C. overnight to evaporate all water. The dried crude product was recrystallized in anhydrous acetonitrile to give white solid which was then dried in a vacuum oven at 100° C. for 48 hours. The characterization results were the same as in Example 5.

EXAMPLE 8

This example illustrates the synthesis of a lithium salt of an orthoborate in which the four boron oxygens are pairwise connected by two methylenedisulfonyl groups, to give an anion of bis(methylenedisulfonato)borate. This compound has a formula lithium bis(methylenedisulfonato)borate. The preparation includes the similar three steps in Example 2, but using methylenedisulfonic acid to replace oxalic acid and di(trimethylsilyl) methylenedisulfonate to replace di(trimethylsilyl) oxalate.

EXAMPLE 9

This example illustrates a method to synthesize the lithium salt of an orthoborate in which the four boron oxygens are pairwise connected by two sulfoacetyl groups, to give an anion of bis(sulfoacetato)borate. This compound has a formula lithium bis(sulfoacetato)borate. The preparation was similar to the second step in Example 4, but using sulfoacetic acid to replace malonic acid.

EXAMPLE 10

This example illustrates the preparation of electrolytic solutions of lithium orthoborate salts, chosen from any of the salts presented hereinabove, in non-aqueous solvents. The non-aqueous solvent is chosen from carbonate, non-carbonate plasticizers or their mixtures. Suitable carbonate plasticizers are, for example, ethylene carbonate (EC), propylene carbonate (PC), butylene carbonate (BC), dimethyl carbonate (DMC) and diethyl carbonate (DEC). Suitable non-carbonate plasticizers are 1,2-dimethoxyethane (DME), 1,2-diethoxyethane (DEE), dimethylsulfoxide (DMSO), dimethyl sulfone (DMS), ethylmethylsulfone (EMS), γ-butyrolactone (BL). Preferred plasticizer mixtures are EC-PC, EC-DMC, EC-DMC-DEC, and PC-DME.

In a dry glove box, a certain amount of lithium orthoborate salt was placed into a volumetric flask and the non-aqueous solvents or solvent mixtures were added. The mixture was shaken occasionally to allow all salt to dissolve and the solution mixing well. The conductivity data of some of these solutions are given in FIGS. 2 to 4.

EXAMPLE 11

This example illustrates the preparation of a gel electrolyte containing lithium bis(oxalato)borate prepared in Example 1.

In a dry glove box, the lithium salt from Example 2 was dissolved in a certain amount of EC-PC (1:1, o/w) mixture in a vial. A quantity poy(methyl methacrylate), PMMA, with high molecular weight of 996,000 was added. The vial was sealed and heated to around 140° C. with occasionally shaking till the mixture was well done. The hot viscous mass was pressed in between two stainless steel plates covered with Teflon films. After cooling, the self-standing membrane was pealed off. The conductivity of the gel electrolyte is given in FIG. 5.

EXAMPLE 12

This example illustrates the electrochemical properties of an electrolytic solution of lithium orthoborate salt from Example 8. The cyclic voltammograms were measured at room temperature on an EG&G potentiostat/galvanostat model 273, with a three-electrode dip-cell with platinum, stainless steel, nickel, aluminum or copper wire as working electrode and lithium metal as counter and reference electrodes. The scan rate was 1 mVs$^{-1}$. The cyclic voltammetric results are given in FIGS. 6 to 8.

EXAMPLE 13

This example illustrates the battery performance of an electrolytic solution of lithium orthoborate salt from Example 10. Prototype lithium rechargeable batteries were assembled by pressing into appropriate cases a sequence of a lithium metal disk anode, a glass fiber film saturated with an electrolytic solution of lithium orthoborate salt from Example 10, and a composite cathode membrane. The latter was a blend of $LiCr_{0.015}Mn_{1.985}O_4$ as the active intercalation material, carbon black as an electronic conductor and PVdF as a polymer binder, in a weight ratio of 82:10:8. The batteries were assembled in a VAC dry box filled with purified argon. Preliminary investigation into the battery characteristics and performance was performed by examining their galvanostatic charge-discharge cyclic curves.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

We claim:
1. An electrolytic salt, comprising:
a formula of

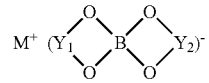

B is boron;
O is oxygen;
C is carbon;
$Y_1$ and $Y_2$ having a chemical bond with a pair of oxygen;
$Y_1$ having a formula XC—$(CR_2)_a$CX, wherein a is 0 to 4, R is a halogen, X is selected from the group consisting of =O, —C=N, CR'$_3$, and R'$_3$, wherein R' is a halogen, when a is 0, then X is $CF_3$;
$Y_2$ having a formula XC—$(CR_2)_a$CX, wherein a is 0 to 4, R is a halogen, X is selected from the group consisting of =O, —C=N, CR'$_3$, and R'$_3$, wherein R' is a halogen, when a is 0, then X is $CF_3$; and
$M^+$ is selected from the group consisting of Group I and Group II elements.

2. The electrolytic salt of claim 1, wherein $Y_1$ consists of the formula $CF_3$—C—$CF_2$—C—$CF_3$.

3. The electrolytic salt of claim 1, wherein $Y_1$ consists of the formula O=C—$CF_2$—C=O.

4. The electrolytic salt of claim 1, wherein X is $CF_3$.

5. The electrolytic salt of claim 1, wherein the electrolytic salt includes a non-aqueous solvent for providing stability.

6. The electrolytic salt of claim 5, wherein the non-aqueous solvent is selected from the group consisting of carbonate, propylene carbonate, butylene carbonate, dimethyl carbonate, diethyl carbonate 1,2-dimethoxyethane, 1,2 -diethoxyethane, dimethylsulfoxide, dimethyl sulfone, ethylmethylsulfone, and γ-butyrolactone and mixtures thereof.

7. The electrolytic salt of claim 1, wherein $M^+$ is lithium.

8. The electrolytic salt of claim 1, wherein $Y_1$ is not $Y_2$.

9. An electrolytic salt, comprising:
a formula of

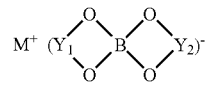

B is boron;
O is oxygen;
C is carbon;
$Y_1$ and $Y_2$ having a chemical bond with a pair of oxygen;
$Y_1$ having a formula O=C—$(CR_2)_a$—C=O, R is a halogen, a is 1 to 4;
$Y_2$ having a formula O=C—$(CR_2)_a$—C=O, R is a halogen, a is 1 to 4; and
$M^+$ is selected from the group consisting of Group I and Group II elements.

10. The electrolytic salt of claim 9, wherein R is fluorine.

11. The electrolytic salt of claim 9, wherein $Y_1$ consists of the formula O=C—$CF_2$—$CF_2$—C=O.

12. The electrolytic salt of claim 9, wherein $Y_1$ consists of the formula O=C—$CF_2$—$CF_2$—$CF_2$—$CF_2$—C=O.

13. The electrolytic salt of claim 9, wherein the electrolytic salt includes a nonaqueous solvent for providing stability.

14. The electrolytic salt of claim 13, wherein the nonaqueous solvent is selected from the group consisting of carbonate, propylene carbonate, butylene carbonate, dimethyl carbonate, diethyl carbonate 1,2-dimethoxyethane, 1,2-diethoxyethane, dimethylsulfoxide, dimethyl sulfone, ethylmethylsulfone, and y-butyrolactone and mixtures thereof.

15. The electrolytic salt of claim 9, wherein $M^+$ is lithium.

16. The electrolytic salt of claim 9, wherein $Y_1$ is not $Y_2$.

17. An electrolytic salt for a battery, comprising:
a formula of

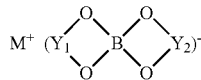

B is boron;
O is oxygen;
C is carbon;
$Y_1$ and $Y_2$ having a chemical bond with a pair of oxygen;
$Y_1$ having a formula $CF_3$—C$(CR_2)_a$C—$CF_3$, wherein a is 1 to 4, R is a halogen;
$Y_2$ having a formula $CF_3$—C$(CR_2)_a$C—$CF_3$, wherein a is 1 to 4, R is a halogen;
$Y_1$ is not $Y_2$; and
$M^+$ is selected from the group consisting of Group I and Group II elements.

18. The electrolytic salt for a battery of claim 17, wherein R is fluorine.

19. The electrolytic salt for a battery of claim 17, wherein $Y_1$ consists of the formula $CF_3$—C—$CF_2$—C—$CF_3$.

20. The electrolytic salt for a battery of claim 17, wherein $Y_1$ consists of the formula $CF_3$—C—$CF_2$—$CF_2$—$CF_2$—$CF_2$—C—$CF_3$.

21. The electrolytic salt for a battery of claim 17, wherein the electrolytic salt includes a non-aqueous solvent for providing stability.

22. The electrolytic salt for a battery of claim 21, wherein the non-aqueous solvent is selected from the group consisting of carbonate, propylene carbonate, butylene carbonate, dimethyl carbonate, diethyl carbonate 1,2-dimethoxyethane, 1,2-diethoxyethane, dimethylsulfoxide, dimethyl sulfone, ethylmethylsulfone, and y-butyrolactone and mixtures thereof.

23. The electrolytic salt for a battery of claim 17, wherein $M^+$ is lithium.

* * * * *

UNITED STATES PATENT AND TRADEMARK OFFICE
CERTIFICATE OF CORRECTION

PATENT NO. : 7,527,899 B2
APPLICATION NO. : 10/311605
DATED : May 5, 2009
INVENTOR(S) : Charles Austen Angell and Wu Xu It is certified that error appears in the above-identified patent and that said Letters Patent is hereby corrected as shown below:

ON THE TITLE PAGE:
Column 2 (Foreign Patent Documents), line 2, delete "DE 198 29 030   10/1999";

Column 2 (Other Publications), line 3, delete "Angell." and insert --Angell,--;

IN THE SPECIFICATION:
Column 1, line 8, delete "Jun. 18,2001" and insert --Jun. 18, 2001--;

Column 1, lines 9-10, delete "Dec. 27,2001," and insert --Dec. 27, 2001,--;

Column 1, line 11, delete "Jun. 16,2000" and insert --Jun. 16, 2000--;

IN THE CLAIMS:
Column 8, line 54 (Claim 6), after "diethyl carbonate" insert --,--.

Column 8, lines 54-55 (Claim 6), delete "1,2 -diethoxyethane," and insert --"1,2-diethoxyethane,--;

Column 9, line 17 (Claim 13), delete "nonaqueous" and insert --non-aqueous--;

Column 9, line 21 (Claim 14), after "diethyl carbonate" insert --,--;

Column 9, line 23 (Claim 14), delete "y-butyrolactone" and insert --γ-butyrolactone--;

Column 10, line 27 (Claim 22), delete "diethyl carbonate" and insert
--diethyl carbonate,--;

Column 10, line 27 (Claim 22), delete "1,2 -dimethoxyethane," and insert
--1,2-dimethoxyethane,--;

UNITED STATES PATENT AND TRADEMARK OFFICE
CERTIFICATE OF CORRECTION

PATENT NO. : 7,527,899 B2
APPLICATION NO. : 10/311605
DATED : May 5, 2009
INVENTOR(S) : Charles Austen Angell and Wu Xu It is certified that error appears in the above-identified patent and that said Letters Patent is hereby corrected as shown below:

Column 10, line 29 (Claim 22), delete "y-butyrolactone" and insert --γ-butyrolactone--.

Signed and Sealed this

Fourteenth Day of July, 2009

JOHN DOLL
*Acting Director of the United States Patent and Trademark Office*